(12) United States Patent
Chen et al.

(10) Patent No.: US 7,352,464 B2
(45) Date of Patent: Apr. 1, 2008

(54) OXYGEN SENSOR FOR AIRCRAFT FUEL INERTING SYSTEMS

(75) Inventors: Shin-Juh Chen, Santa Fe, NM (US); Joel A. Silver, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 133 days.

(21) Appl. No.: 11/029,436

(22) Filed: Jan. 4, 2005

(65) Prior Publication Data

US 2005/0286054 A1 Dec. 29, 2005

Related U.S. Application Data

(60) Provisional application No. 60/612,705, filed on Sep. 24, 2004, provisional application No. 60/546,526, filed on Feb. 19, 2004, provisional application No. 60/534,544, filed on Jan. 5, 2004.

(51) Int. Cl.
*G01N 21/00* (2006.01)
(52) U.S. Cl. .................................. 356/437; 356/439
(58) Field of Classification Search ................. 356/437
See application file for complete search history.

(56) References Cited

U.S. PATENT DOCUMENTS 5,572,031 A 11/1996 Cooper et al.
6,064,488 A * 5/2000 Brand et al. ................ 356/440
6,634,598 B2 10/2003 Susko

OTHER PUBLICATIONS

Bomse, David S., et al., "Frequency Modulation and Wavelength Modulation Spectroscopies: Comparison of Experimental Methods Using a Lead-Salt Diode Laser", *Applied Optics*, vol. 31, No. 6, (Feb. 20, 1992),718-731.
Chen, Shin-Juh , et al., "Detection of Explosive Mixtures in the Ullage of Aircraft Fuel Tanks", *42nd AIAA Aerospace Sciences Meeting and Exhibit*, Reno, Nevada, Paper 2004-0545,(Jan. 5-8, 2004).
Edwards, D. , et al., "Interfacial Transport Processes and Rheology", *Text. Butterworth-Heinemann*, Boston MA, (1991),161-185.
Herriott, Donald R., et al., "Folded Optical Delay Lines", *Applied Optics*, vol. 4, No. 8, (Aug. 1965),883-889.
Herriott, D. , et al., "Off-Axis Paths in Speerical Mirror Interferometers", *Applied Optics*, vol. 3, No. 4, (Apr. 1964),523-526.
MacManus, J. B., et al., "Astigmatic Mirror Multipass Absorption Cells for Long-Path-Length Spectroscopy", *Applied Optics*, vol. 34, No. 18, (Jun. 20, 1995),3336-3348.

(Continued)

*Primary Examiner*—Gregory J. Toatley, Jr.
*Assistant Examiner*—Amanda H Merlino
(74) *Attorney, Agent, or Firm*—Jeffrey D. Myers; Samantha A. Updegraff; Peacock Myers, P.C.

(57) ABSTRACT

An apparatus and method for monitoring oxygen concentrations in fuel tank ullage comprising providing a sensor head comprising an optical cavity, exposing the optical cavity to an ambient gaseous environment of a fuel tank or air separation module, via a laser light source emitting wavelength modulated light through the cavity, and receiving the wavelength modulated light with a detector.

22 Claims, 6 Drawing Sheets

OTHER PUBLICATIONS

Reynolds, Thomas L., et al., "Onboard Inert Gas Generation System/Onboard Oxygen Gas Generation System Study", *Part II: Gas Separation Technology—State of the Art*; NASA CR-2001-210950, (Aug. 2001),1-60.

Rothman, L. S., et al., "The HITRAN Molecular Spectroscopic Database: Edition of 2000 Including Updates throu 2001", *Journal of Quantitative Spectroscopy & Radiative Transfer*, vol. 82, (2003),5-44.

Silver, Joel A., "Frequency-Modulation Spectroscopy for Trace Species Detection: Theory and Comparison Among Experimental Methods", *Applied Optics*, vol. 31, No. 6, (Feb. 20, 1992),707-717.

White, John U., "Long Optical Paths of Large Aperture", *Journal Optical Society Am.*, vol. 32, (May 1952),285-288.

* cited by examiner

OXYGEN SENSOR FOR AIRCRAFT FUEL INERTING SYSTEMS

CROSS-REFERENCE TO RELATED APPLICATIONS

This application claims the benefit of the filing of the following U.S. Provisional Patent Applications: Ser. No. 60/534,544, entitled "An oxygen sensor for monitoring the ullage of liquid fuel tanks," filed on Jan. 5, 2004; Ser. No. 60/546,526, entitled "An oxygen sensor for monitoring on-board inert gas generation system and ullage of fuel tanks in aircraft," filed on Feb. 19, 2004; and Ser. No. 60/612,705, entitled "An oxygen sensor for aircraft fuel inerting systems," filed on Sep. 24, 2004. The specifications thereof are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DMI-0319786, awarded by the National Science Foundation.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to the detection of oxygen in aircraft fuel inerting systems including the monitoring of the output of inerting gas from an air separation module of an on-board inert gas generation system, and the monitoring of oxygen content in the ullage (gas space between liquid fuel surface and top of fuel tank interior) of aircraft fuel tanks.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The effective prevention and control of fires and explosions originating in fuel systems during in-flight, maintenance, and post-crash are critical for both commercial and military aircraft. As liquid fuel is consumed, a space (also called ullage) containing air and fuel vapor is developed above the liquid fuel. This fuel-air mixture is potentially dangerous if a combustible or explosive composition coupled with favorable environmental factors and an ignition source are present. Methods to reduce the oxygen concentration in this fuel-air mixture are necessary for the survivability of both commercial and military aircraft. These methods typically displace the oxygen inside the ullage with nitrogen. Moreover, monitoring systems are also needed to accurately determine the oxygen content inside the ullage and the quality of the inerting gas (S.-J. Chen, et al., "Detection of explosive mixtures in the ullage of aircraft fuel tanks," 42nd AIAA Aerospace Sciences Meeting and Exhibit, Reno, Nev., AIAA Paper No. 2004-0548, January 2004).

Replacing the fuel vapor-laden space (ullage) inside the fuel tank as the liquid fuel is being consumed with nitrogen-enriched air (NEA) minimizes fires and explosions due to potential ignition sources such as lightning strikes, artillery shells, static discharge, wiring sparks, and heating sources. Air separation technologies for the air separation module (ASM) include pressure swing adsorption, hollow fiber membrane, ceramic membrane, and cryogenic air separation. The NEA usually contains more than 90 percent nitrogen. The ullage oxygen concentration is recommended to be between 9-12 percent to eliminate potential in-tank fires and explosions due to all possible ignition sources (T. L., Reynolds, et al., "Onboard inert gas generation system/ onboard oxygen gas generation system (OBIGGS/OBOGS) study, Part II: Gas separation technology—State of the art," NASA CR-2001-210950, 2001).

An onboard inert gas generation system (OBIGGS) generally encompasses an ASM to generate NEA, a compressor, storage tanks, and a distribution system. The military has OBIGGS currently installed in the AH-64, C-5, C-17, F-22, and V-22 aircraft to reduce oxygen levels below the lower explosive limit inside the fuel tanks. From 1959 to 2001, seventeen commercial aircraft experienced fuel tank explosions that resulted in 542 fatalities worldwide (Aviation Rulemaking Advisory Committee, "Service history/fuel tank safety level assessment," Task Group 1, 14 Jul. 1998; www.ntsb.gov/Pressrel/2001/010411.htm). OBIGGS is currently being considered for commercial aircraft to reduce the likelihood of in-tank fires and explosions. Ground and flight tests are already underway to design effective inerting systems for the commercial aircraft. Oxygen sensors for monitoring the NEA exiting the ASM of OBIGGS and inside the ullage are required to fully assess the effectiveness of inerting systems and the safety of fuel tanks. Oxygen sensors used in military aircraft are based on zirconium oxide and operate at a high temperature that is not suitable for commercial aircraft due to the potential ignition hazard from the sensor itself.

D. E. Cooper, et al., "Pressure, and temperature-compensating oxygen sensor," U.S. Pat. No. 5,572,031 (1996), disclose an optically-based absorption spectroscopy with frequency modulation to measure oxygen concentrations in aircraft fuel tanks. The RF modulation frequency is in the MHz range, and demodulation frequency is at an integral multiple of the modulation frequency. The sensor system contained a reference cell for line-locking and calibration purposes, and a sample cell that is covered with a gas permeable membrane to prevent liquid fuel from entering the said cell. The pressure in the reference cell is derived from the measurement of temperature inside the cell. Temperature and pressure sensors are located in the sample cell.

K. Susko, "On-board fuel inerting system," U.S. Pat. No. 6,634,598 (2003), discloses an nitrogen inerting system to reduce combustible and explosive mixtures that could be present in the ullage of aircraft fuel tanks. A fiberoptic probe based on chemical fluorescence actively monitors the partial pressure of oxygen in the ullage. The sensor probe does not introduce electrical current into the fuel tank. The head of the sensor probe is shielded from the liquid fuel using a gas permeable membrane or a baffle system. The whole sensor probe needs to be maintained within a narrowly defined band of temperature to assure accurate oxygen readings. This temperature is usually above the maximum temperature that the aircraft encounters during its operation either on the ground or in-flight.

The present invention improves on the art by using an optically-based oxygen detection system that comprises a widely-tunable diode laser, a photodiode detector, a measurement cell that is open to the environment, beam forming optics, liquid immersion prevention mechanisms, liquid removal mechanisms, and a digital signal processor-based electronics. The present invention does not require a reference cell for line-locking the laser wavelength or calibrating the sensor; wavelength modulation (kHz) instead of frequency modulation (MHz) is used; the measurement cell is open to the environment being measured to allow both liquid and gas to easily pass through, thus eliminating any diffusion time that is required of a gas permeable membrane; means for monitoring the integrity of the senor head and laser system are implemented; and means for providing a control feedback mechanism to the OBIGGS is incorporated. The invention is preferably used to monitor oxygen concentrations in the ullage of aircraft fuel tanks and/or at the outlet of an ASM.

BRIEF SUMMARY OF THE INVENTION

The present invention is of an apparatus and method for monitoring oxygen concentrations in fuel tank ullage, comprising: providing a sensor head comprising an optical cavity; exposing the optical cavity to an ambient gaseous environment of a fuel tank or air separation module; via a laser light source, emitting wavelength modulated light through the cavity; and receiving the wavelength modulated light with a detector. In the preferred embodiment, the laser light source comprises a diode laser light source emitting wavelength modulated light modulated about an absorption wavelength of oxygen, most preferably wherein the laser light source comprises a vertical cavity surface emitting laser light source. The detector preferably comprises a photodiode detector. One or both of measuring pressure of the ambient gaseous environment and measuring temperature of the ambient gaseous environment should be employed. The optical path in the cavity is extended, preferably via one or more of the group consisting of off-axis parabolic mirrors, retroreflectors, and multiple pass cells. A sealed reference cell is preferably provided containing a predetermined concentration of oxygen, together with a beamsplitter capturing a portion of the wavelength modulated light and directing it through the reference cell and a second detector receiving the portion. The laser light source can comprise a fiber optic emission point. Removal of liquid droplets is expedited from surfaces through which the wavelength modulated light passes. One or more sealed chambers housing the laser light source and the detector can be employed, preferably together with a beamsplitter to capture a portion of the wavelength modulated light and direct it through the one or more chambers but not outside of the one or more chambers and reception of the portion with a second detector. The optical cavity is preferably encased at least partially in a metal foam.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of a sensor system that can continuously monitor oxygen concentrations in aircraft fuel inerting systems which comprise an on-board inert gas generation system and fuel tank. The oxygen sensor system preferably comprises: a sensor head that is inside the fuel tank or in-line with the ASM outlet to monitor oxygen concentrations; an electronics module for controlling the sensor head, acquiring and processing data; and a reporting mechanism for visual and audible warnings to the pilot and a feedback control parameter to the inerting system. The invention can monitor oxygen concentrations inside the ullage of aircraft fuel tanks and/or in-line at the outlet of an air separation module for an onboard inert gas generation system, without the need of a reference cell, with a measurement cavity that is open to the environment being measured, with means to minimize optical degradation due to splashing liquid fuel and liquid droplets depositing on optical windows, with means to check the integrity of the sensor head and health of the light source, and with means to transmit the oxygen measurements to the crew and/or inerting systems for warning purposes and feedback controls.

In the preferred embodiment the sensor head comprises: a diode laser for generating the required absorption wavelength for oxygen; a photodiode detector for collecting the laser light after it has traversed the open cavity of the measurement cell; an optical setup for directing the laser beam across the measurement cell for optimum optical path length; mechanism to minimize liquid splashing on the optical surfaces; mechanism to enhance the removal of liquid droplets off the optical surfaces; and pressure and temperature sensors for quantifying the measurements.

Objects of the present invention include: (1) providing a means to monitor the oxygen concentrations in the ullage and ASM outlet of aircraft inerting systems; (2) providing a method to measure chemical species concentrations based on optical absorption spectroscopy with wavelength modulation to increase sensitivity of the measurements; (3) providing a means to minimize optical interferences due to liquid droplets impinging on the optical surfaces when the sensor head is inside the fuel tank; (4) providing a means to warn the pilot of explosive mixtures present inside the fuel tank and provide a feedback mechanism to the OBIGGS; and (5) providing a means to check the integrity of the sealed chambers in the sensor head, and the integrity and health of the laser.

Advantages of this approach include that oxygen concentrations inside the fuel tank and the quality of inerting gas can be monitored in near real-time, and that the sensor system is rugged and intrinsically safe for operation in fuel vapor-laden spaces. The oxygen concentration is preferably reported every second, but other averaging times that are shorter or longer than one second are all within the reach of this sensor system. A longer averaging-time will give measurements with lower noise, and thus higher accuracy can be achieved. A one-second averaging time is more than sufficient to achieve the sensitivity and accuracy required by the sensor system for application either in-tank or in-line with the ASM outlet.

The sensor system when installed at the ASM outlet and in the fuel tanks can provide a closed-loop system for the operation of OBIGGS. Oxygen concentrations in the fuel tanks are fed to the OBIGGS and decision is made as to whether to continue flowing the inert gas into the fuel tanks. Furthermore, the oxygen sensor installed at the ASM outlet can monitor the health of the inerting system, and warn the pilot of any irregularities of the system.

To reiterate, the invention is of a method of and apparatus for detecting oxygen concentrations in aircraft fuel inerting systems which include monitoring the inerting gas generated by the on-board inert gas generation system and monitoring the ullage of fuel tanks. It can operate in the conditions experienced during flight and the conditions encountered in an aircraft fuel tank and ASM outlet. Having the sensor system inside the fuel tank provides the best and most direct approach to assess fire and explosion hazards. Existing technologies based on electrochemistry, fluorescence quenching, and paramagnetic properties of oxygen for measuring oxygen concentrations are not suitable for aircraft fuel tanks because the presence of fuel vapor in the ullage prevents safe sensor operation and inhibits optimal performance. Zirconium oxide sensors are used to monitor the quality of NEA at the ASM outlet for military aircraft. However, these sensors cannot be used in commercial aircraft since the sensor operates at high temperature and can be an ignition hazard.

The measurement of chemical species concentrations by diode laser optical absorption is based on an implementation of Beer's law. This method is a line-of-sight technique, so the absorbances (ratio of the change in light intensity to incident light intensity) are always spatial integrals along the optical path. Because the quantity actually measured is the ratio of incident light intensity to transmitted light intensity, the resulting concentration is independent of any laser intensity fluctuations and depends only on accurately-known parameters. High-sensitivity is achieved by using wavelength modulation spectroscopy (WMS) to shift the detection band from DC (where laser amplitude noise can obscure weak absorbances) to high frequencies where laser excess (1/f) noise is unimportant (J. A. Silver, "Frequency modulation spectroscopy for trace species detection: theory and comparison," Appl. Opt. 31, 707-717, 1992; and, D. S. Bomse, et al., "Frequency modulation spectroscopy for trace species detection: experimental comparison of methods," Appl. Opt. 31, 718-731, 1992). Fractional absorption sensitivities near the shot-noise limit ($\sim 10^{-7}$) can be achieved. Field measurements using WMS routinely maintain minimum detection absorbances of better than $10^{-5}$ (at 1 Hz bandwidth) for extended (many month) operation. For comparison, direct transmission methods such as FTIR are only capable of detecting $10^{-3}$ absorbances. To implement WMS, a small sinusoidal modulation at frequency f is superimposed on the diode laser injection current. This current modulation produces a modulation of the laser wavelength, since wavelength is tuned by changing the current. The amplitude of the current modulation is chosen so that the induced wavelength modulation is comparable to the width of the spectral feature under study. Absorption by the target gas converts the laser wavelength modulation to an amplitude modulation that induces AC components in the detector photo-current. Phase-sensitive electronics are then used to demodulate the detector photo-current at a selected harmonic, nf (typically, n=2). Detection frequencies as low as 20 kHz are often sufficient to bypass laser excess noise. The signal from this detection method appears as approximately the second derivative of the absorption feature with respect to wavelength. To a first order, diode lasers have linear current versus intensity curves. Thus, 2f signals have a zero background.

The HITRAN database (Rothman, et al., "The HITRAN molecular spectroscopic database: edition of 2000 including updates of 2001, J. Quant. Spectrosc. Radiat. Transfer 82, 5-44, 2003) shows well-resolved individual absorption lines in the oxygen absorption band in the 762 to 766 nm (13,055-13,123 cm$^{-1}$) spectral region. This spectral region is generally inactive and is free of interference from other ambient (e.g., nitrogen and water vapor) and fuel species. One important advantage of an optical detection approach is that fuel vapor does not introduce background absorbance signals. This occurs for two reasons. First, hydrocarbons do not have significant absorption bands in the near-visible spectral region (~760 nm). Second, the very weak bands that might occur are spectrally broad and diffuse, whereas the WMS methods are sensitive only to sharp spectral features as seen in the absorption band noted earlier.

The preferred apparatus to conduct the measurement of oxygen comprises a diode laser, silicon photodiode, and pressure and temperature sensors. A recent innovation in diode lasers is the development of vertical cavity surface emitting lasers. VCSELs emit upwards from the semiconductor layers deposited on a substrate and as a result are easier to produce, can be tested during fabrication and can be more densely packed, thus lowering costs. Presently, these types of lasers are commercially available at wavelengths between 750 and 2050 nm (4,878-13,333 cm$^{-1}$). Research leading to the formation of a number of new commercial enterprises is rapidly pushing the range of wavelengths towards both the UV (shorter wavelengths) and near-infrared (longer wavelengths). VCSELs are extremely efficient and require only between 3 and 10 mA to operate. They can tune over 10 to 50 cm$^{-1}$ of wavelength, have collimated circular beams, and have output powers near 0.5 mW, which is more than sufficient for gas sensing via wavelength modulation spectroscopy. A consequence of the wide tunability of a VCSEL is that selection of the optimal absorption line and/or detection of multiple lines or gases is possible using a single laser. Size, optical and power requirements are significantly reduced as well. VCSELs have been shown to operate in environmental temperatures ranging from 60 to +60° C., and pressures as low as 20 Torr; thus, making these VCSELs suitable for operation in flight.

Pressure and temperature alter the line width and magnitude of the absorption feature. Pressure and temperature information at the measurement location are required. These spectral changes can be divided into two categories: pressure broadening of the line shape and temperature changes in the line strength. Pressure broadening affects the line width (which varies linearly with pressure) and the line shape. The line shape changes are mainly observed in the wings of the absorption. By excluding the wings of the absorption in the fit (staying within the trough to trough region in the 2f spectrum), the line shape changes can be minimized. Temperature can be easily obtained using a thermistor embedded into the wall of the sensor system. Moreover, temperature can be obtained spectroscopically as well by using line ratios of two absorption lines, or fitting a series of measured absorption lines to theoretical ones. The R-branch of the oxygen absorption band in the 759 to 762 nm (13,123-13,175 cm$^{-1}$) is an excellent candidate. Pressure can be obtained from the avionics since the pressure differential between the ambient and in-tank conditions is about 0.25 psi at cruise conditions (worst-condition). Moreover, another method to obtain pressures is through spectroscopic means, or using an in situ pressure probe that is protected from liquid fuel using a gas permeable membrane.

The oxygen sensor system preferably comprises a sensor head, control electronics module, and a status display. The sensor head is mounted inside the aircraft fuel tank for in-situ oxygen measurements in the ullage and/or in-line with the ASM outlet for monitoring the quality of the inerting gas.

Figure 1:
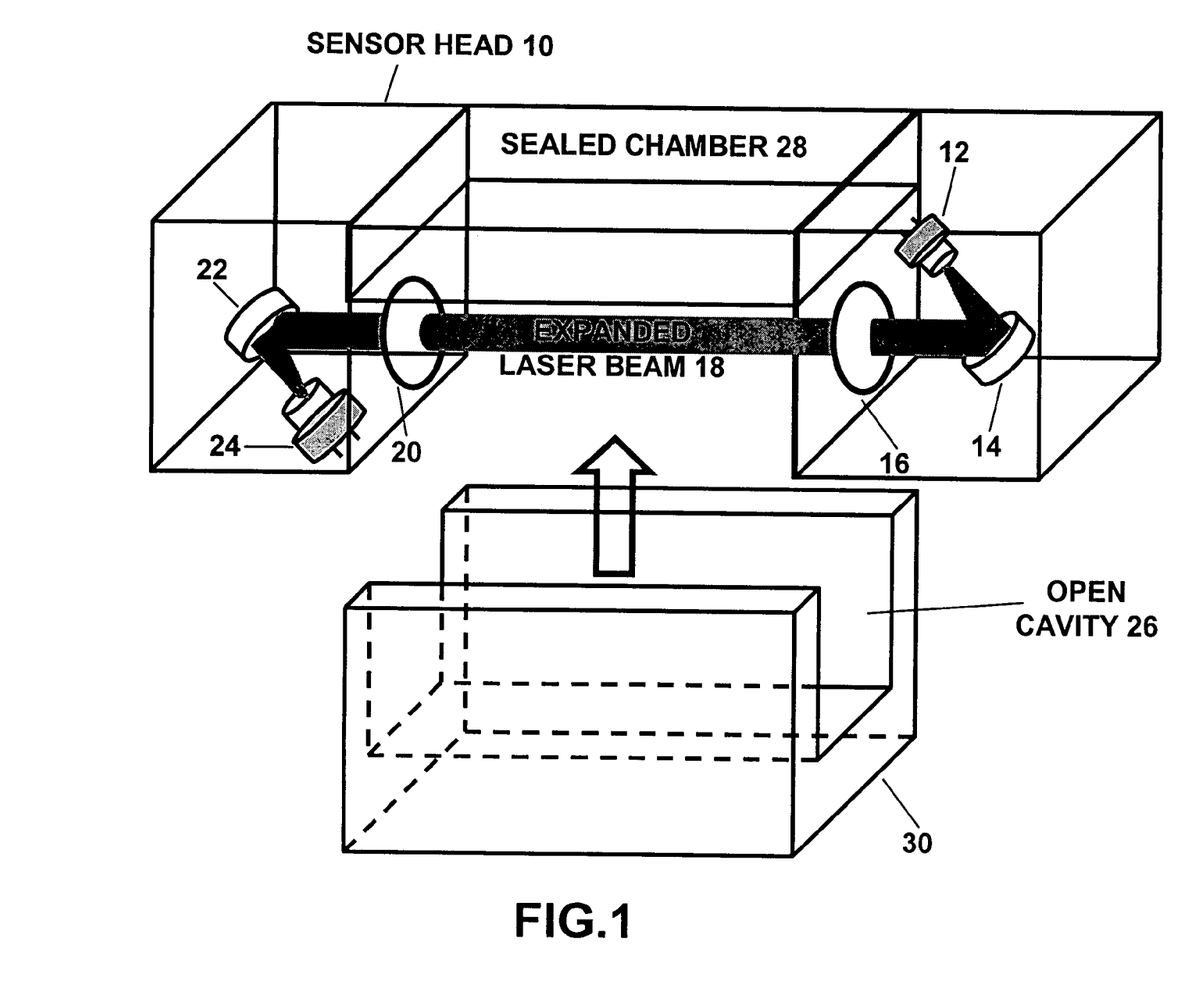
FIG. 1 is a 3-D schematic diagram of the preferred embodiment of an in-tank oxygen sensor system showing an expanded laser traversing a measurement cavity enclosed by a metal foam, and two off-axis-parabolic (OAP) mirrors to direct light into the cavity and onto a photodiode detector.

The invention provides a means to generate the required optical path length for the absorption-based optical spectroscopy. In a preferred embodiment of the sensor head 10, the laser light beam from a diode laser 12 is expanded by an off-axis parabolic mirror (OAP) 14. The diode laser 12 is located near the focal point of the OAP 14. The expanded beam 18 then traverses the measurement cavity 26 by passing through an optical window 16 (e.g., made of sapphire, quartz) and re-entering the sealed chamber 28 through another optical window 20 (e.g., made of sapphire, quartz). The expanded beam 18 is then refocused by another OAP 22 onto a silicon photodiode detector 24. An expanded beam is less susceptible to degradation from the deposits of liquid droplets on optical surfaces that might prevent any laser signal to reach the photodiode detector 24. A large area photodiode detector is preferred for collecting any laser light that reaches the detector. The measurement cavity 26 is open and contains a volume of the ullage gases. The two optical windows 16 and 20 are slightly angled inward toward each other for two main purposes. One is to allow the drainage of liquid fuel droplets that might have been deposited on the window, and the other is to minimize the generation of optical interference fringes (étalons). A hermetically-sealed chamber 28 houses the photodiode detector 24 and the laser diode 12. The chamber contains an inert gas (e.g., nitrogen, argon) which does not interfere with the measurement of oxygen. Only the optical windows 16 and 20 come into contact with the measurement environment.

The invention further provides a means to protect the optical windows located inside the measurement cavity from splashing liquid when the sensor head is installed in the ullage of aircraft fuel tanks. During a typical operation of an aircraft, unsteady motions (due to atmospheric turbulence, sudden acceleration and de-acceleration) can modify the structure of the liquid layer inside the fuel tank. Even if the sensor probe was flush with the top wall of the fuel tank, scenarios of liquid splashing onto the sensor probe are still possible. The liquid layer can move back and forth, filling up certain sections of the tank while emptying others. Sloshing motions with various amplitude and frequency can develop. Preventing the optical windows from getting wet is important to minimize the degradation of the sensor's performance. However, any preventive measure must not considerably degrade the time response of the sensor to the changes in oxygen concentration inside the fuel tank (such as during inerting). As shown in FIG. 1, a highly porous metal foam 30 which can allow both liquid and gas to pass through is an excellent choice for stopping liquids droplets from reaching the optical windows 16 and 20 of the sensor head 10 during fuel sloshing scenarios. The measurement cavity 26 is enclosed in such a metal foam with an interior cavity for the laser beam to travel unobstructed across this open cell for the purpose of optical absorption measurements. When the metal foam 30 is lowered into a pool of liquid fuel, liquid fills the pores of the foam immediately; this demonstrates the high porosity of the said foam. As liquid splashes onto the said metal foam, the foam absorbs the impact energy of the liquid. The liquid droplets do not fully penetrate the wall of the foam 30 to reach the interior of the measurement cavity 26. The liquid fills the pores inside the metal foam, and drains off quickly. The shape of the metal foam as illustrated in FIG. 1 can be of other geometrical shapes. For example, the bottom side of the foam can be a half cylinder, or the foam can be a hollow cylinder with a side portion cut away.

Figure 2:
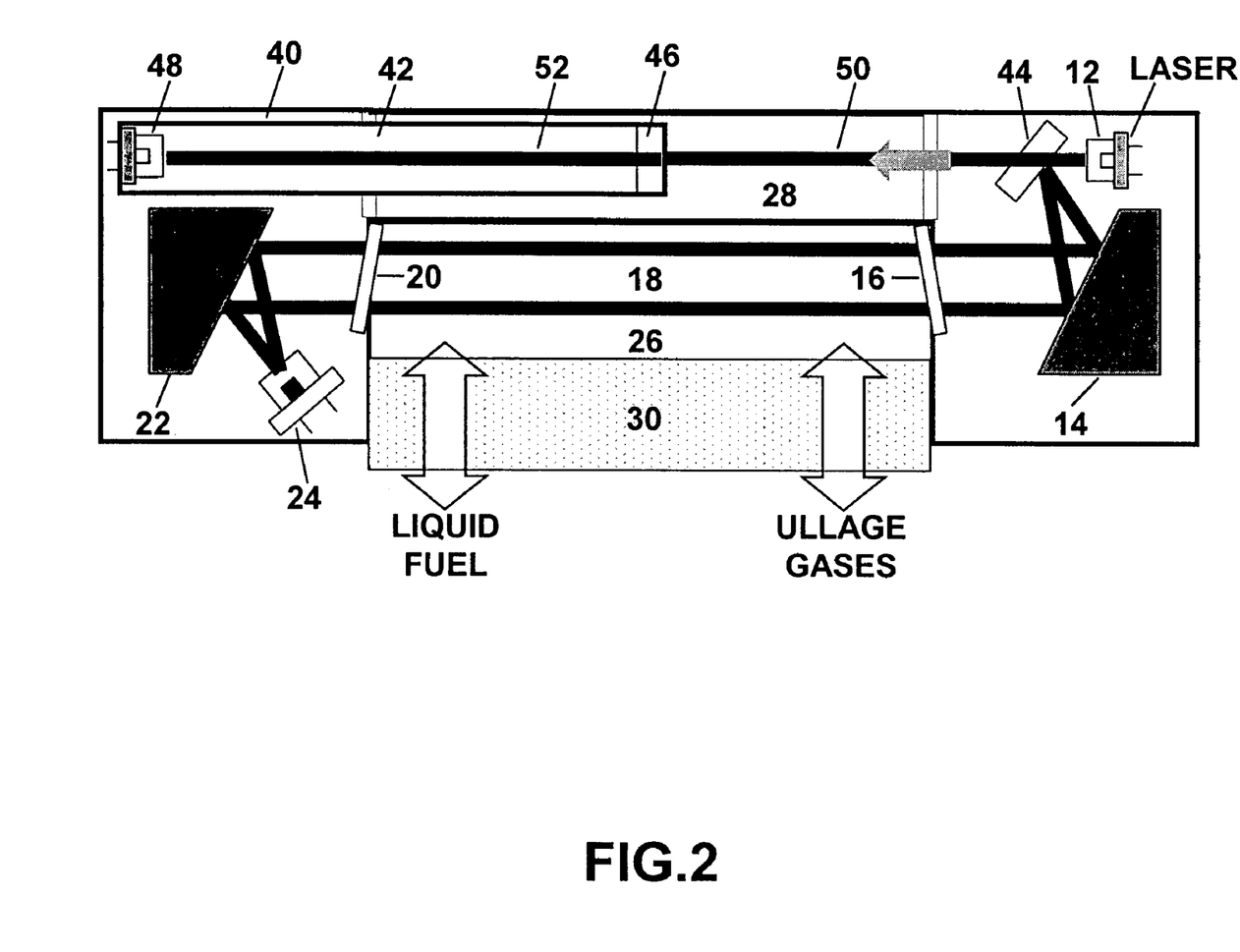
FIG. 2 is a schematic diagram showing a modification to the preferred embodiment by incorporating a reference cell that contains a known oxygen concentration for line-locking purposes in environment where ambient oxygen levels are too low, the laser signal is too noisy, or rapid recovery from a liquid immersion is necessitated.

A modification to the preferred embodiment of the sensor head (FIG. 2) is to include a sealed reference cell 40 that contains a gas mixture 42 (e.g. oxygen with nitrogen) with predetermined oxygen concentration for line-locking the laser operating wavelength in environments where the level of oxygen is insufficient for effective line-locking or the laser signal is very noisy. This level will depend on the inherent sensitivity of the sensor system. In most cases, the level of oxygen where a reference cell might become necessary is less than 1 percent. A reference cell is also useful for cases of complete liquid immersion of the sensor system where the laser signal will be temporarily lost. The reference cell 40 will prevent this temporary loss of the operating wavelength. An optical window 46 (e.g., made of sapphire) is secured to one end of the reference cell 40, and a silicon photodiode detector 48 is secured at the other end of it. A pellicle beamsplitter 44 directs the laser beam into two separate paths. Other types of beam splitters can be used as well. In the first path 50 and 52, the laser beam passes through the pellicle beamsplitter, the optical window 46 of the reference cell 40, the reference gas 42, and ends at the silicon photodiode detector 48. In the second path 18, the expanded laser beam reflects off the pellicle beamsplitter 44, and the first OAP 14 directs the laser beam into the measurement cavity 26 by passing through two optical windows 16 and 20 that are in contact with the ullage environment. The expanded laser beam then reflects off another OAP 22 and focuses the beam onto another silicon photodiode detector 24. The metal foam 30 minimizes the effects of sloshing fuel on the optical sampling area 26. The reference cell 40 is not needed for in-tank application of the sensor system since the level of oxygen (up to 9-12 percent in a fully inerted tank) present in the ullage of fuel tank is more than adequate for line-locking the laser wavelength. For the in-line application at the ASM outlet, the reference cell 40 is also not needed since the inerting gas usually contains a few percent of oxygen. As long as the ambient oxygen level is above one percent with an achievable resolution of $\frac{1}{10}$ percent, a reference cell may not be required.

A robust wavelength search mechanism can be implemented into the laser system to recover the initial operating laser wavelength without the use of a reference cell in case of frequent immersions. This search mechanism essentially re-adjusts the laser operating temperature since the laser is tuned (in wavelength) by changing its operating temperature. When the absorption line is not centered in its spectral scan, the temperature is adjusted to re-center it. The off-centering is caused by a drift in the laser temperature. When an immersion scenario of the sensor head occurs, the current laser operating temperature is recorded. When the sensor head recovers from the immersion, line-locking is rechecked immediately. If line-locking is lost, then the current laser operating temperature is compared to the recorded one which was obtained prior to the immersion. The difference in operating temperature is reduced by readjusting the current laser operating temperature. This search mechanism is effective and realizable when the laser operating environment does not experience sudden changes in temperature. Note that sudden temperature changes in the measurement cell have no effect on the laser operating wavelength.

Figure 3:
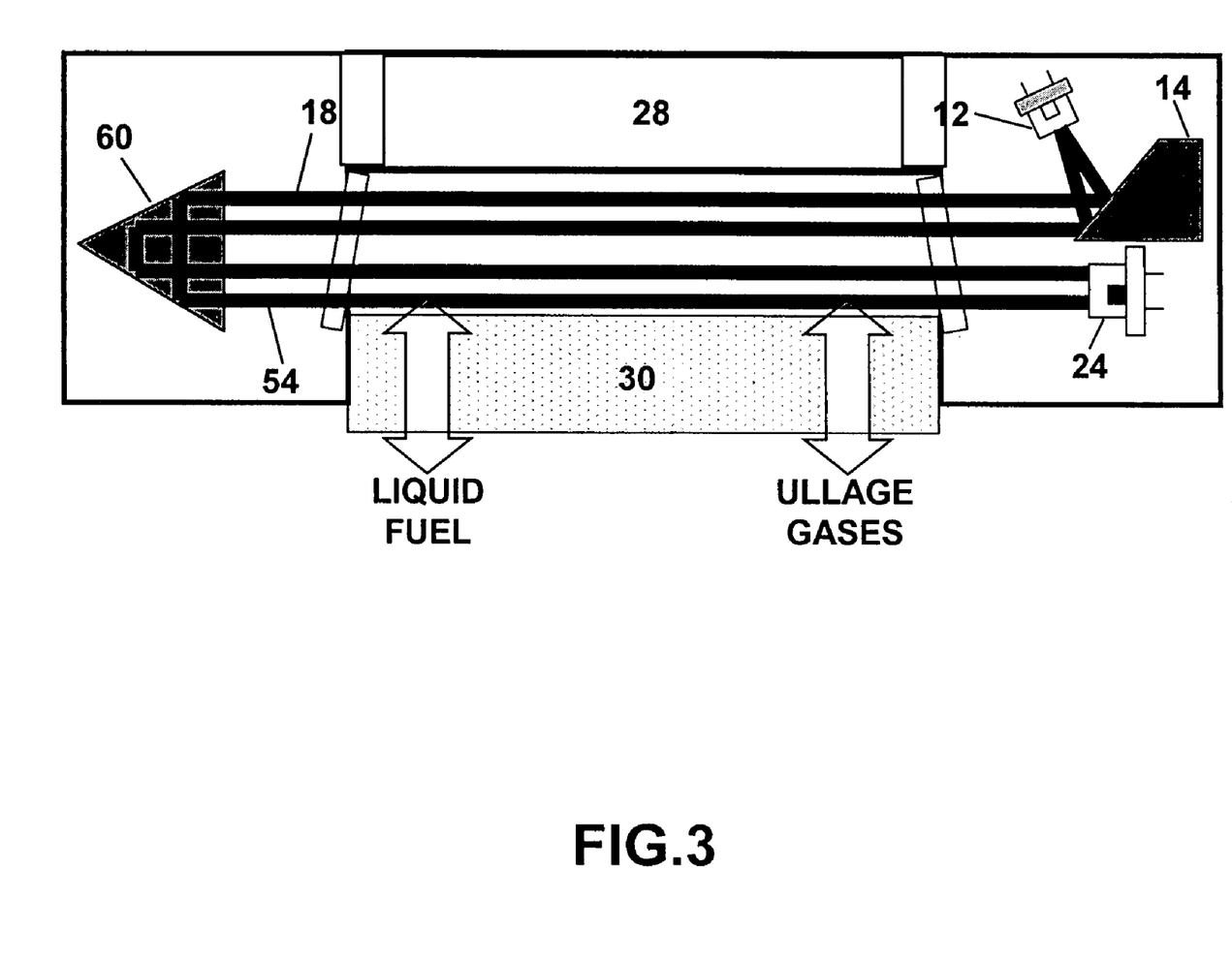
FIG. 3 is a schematic diagram showing an alternative to the preferred embodiment by doubling the total optical path length by replacing one of the OAP's with a retro-reflector.

An alternative to the preferred embodiment of the sensor head (FIG. 3) is to double the total optical path length (thus doubling the sensitivity) by replacing the left OAP 22 in FIG. 1 with a retro-reflector 60. The laser beam 18 after traversing the measurement cavity 26 once will then return to the right-hand side of the chamber by reflecting off the retro-reflector 60, and the reflected laser beam 54 traverses the measurement cavity 26 one more time before being collected by a photodiode detector 24.

Figure 4:
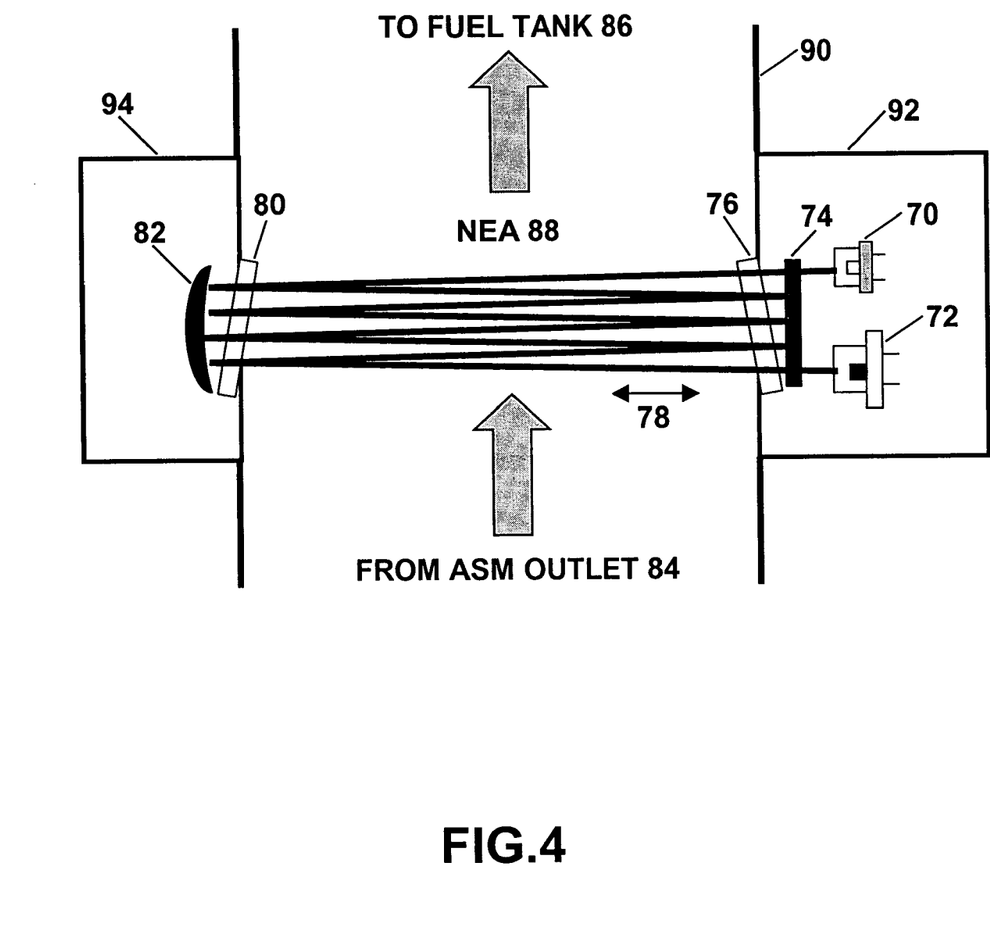
FIG. 4 is a schematic diagram showing another alternative to the preferred embodiment, applied in the outlet of an ASM, by using a multiple-pass cell in which the laser beam is bounced back-and-forth several times between two mirrors to generate a long optical path length.

Another alternative to the preferred embodiment of the sensor head (FIG. 4) is that the total optical path length can be further increased by using a multiple-pass cell 78 in which the laser beam is bounced back-and-forth between two mirrors 82 and 84, which are protected by optical windows 76 and 80, to generate a long path length. One sealed chamber 94 houses a mirror 82. Another sealed chamber 92 houses the laser diode 70, photodiode 72, and another mirror 74. The two sealed chambers 92 and 94 contain an inert gas. These multiple-pass cells can be based on the designs of D. R. Herriott, et al., "Off-axis paths in spherical mirror interferometers," *Appl. Opt.* 3, 523-526, 1964; J. U. White, *J. Opt. Soc. Am.* 32, 285, 1942; astigmatic cells by D. R. Herriott, et al., "Folded optical delay lines," *Appl. Opt.* 4, 883-889, 1965, and by J. B. MacManus, et al., "Astigmatic mirror multipass absorption cells for long-path-length spectroscopy," *Appl. Opt.* 34, 3336-3348, 1995. In a Herriott-type cell, circular patterns of laser pots are obtained on the reflecting surfaces. The photodiode detector and the laser diode can be located on the same or opposite side. A hole is typically drilled through one mirror to inject the laser beam into the measurement cell, and to collect the incoming laser beam after it has traversed the measurement cell several times and exits onto a photodiode detector. The laser and the photodiode detector can share the same hole. An alternate setup is to have two holes on one of the reflecting surfaces or one hole on each of the said surfaces. This multiple-pass measurement cell 78 is appropriate for an in-line ASM outlet 84 application where liquid droplets are not present during the normal operation of the inerting system. Because this design can readily accommodate 40 or more passes, a long optical path can be achieved within a very compact footprint. This feature could be implemented for the oxygen monitoring of ASM outlet gases. High accuracy measurements will require long optical path lengths for an absolute precision of 0.01 percent, for example. This in-line sensor head 90 can be easily adapted to an ASM outlet 84 to provide NEA 88 to the fuel tank 86. In the setup shown in FIG. 4, the photodiode 72 and laser 70 are mounted on separate holes drilled through the flat mirror 74.

In another embodiment of the oxygen sensor system, the laser beam can be brought into the measurement chamber via a fiber optic from the electronics module and return to the electronics module via another fiber optic to a photodiode detector. In this embodiment, the sensor head contains only beam forming and collecting optics. There are no electrical components inside the sensor head. Aircraft fuel tanks are composed of several fuel compartments. For example, the center-wing tank of Boeing 747 aircraft has six interconnected fuel compartments. Additional fuel compartments are located in both wings of the aircraft. Although the discussion of the present invention has focused mainly on a single fuel tank compartment, it is obvious to the practitioners in the field that the present invention can be extended to a distributed oxygen sensor system to monitor several compartments in the fuel tanks simultaneously. Moreover, a single fiberized laser system with a beam splitter could provide light to several sensor heads that are distributed over several fuel compartments.

The invention also provides for a means for enhancing the removal of liquid droplets from the windows in scenarios of liquid immersion when the sensor head is operating inside the ullage of aircraft fuel tanks. These liquid removal mechanisms can be either active or passive. Passive mechanisms preferably comprise: modifying the characteristics of window surfaces by applying coatings and improving the smoothness of window surface); orienting the windows so as to promote liquid drainage through the agglomeration of small droplets as they slide over the window with their motion driven by gravitational or external forces; and taking advantage of external forces that are present during flight which include engine vibrations and atmospheric turbulence. Active mechanisms preferably comprise: surface blowing using ullage gases to blow unto the optical surfaces to remove liquid droplets; spinning/shaking of optical surfaces using a motor driven by pressurized inerting gas or electrical power to spin the surface; and spot warming or cooling using a thermoelectric cooler attached to the surface to promote bulk fluid motion due to the application of local heating or cooling. Such fluid motion driven by the spatial variation in surface tension, which was induced by thermal gradients at the liquid-surface interface, is termed Marangoni flow (D. Edwards, et al., "Interfacial transport processes and rheology," Butterworth-Heinemann, Boston, Mass., 161-185, 1991) in the fluid dynamics literature.

In addition, the invention provides for a means to control, acquire, and process the collected data through an electronics module during the operation of the oxygen sensor system. Complete control of the laser (including waveform generation), WMS, data acquisition, and analysis can be accomplished using a custom digital signal processor (DSP) system. Data analysis algorithms can be implemented into the DSP system for a real-time readout of concentrations. The laser controller board includes all the features needed to operate the laser and to collect data from the detectors. The board operates from a widely used DSP, which can be programmed in C. The board electronics modulate the laser wavelength with a sine wave, and simultaneously ramps the laser wavelength so that the spectral line shape can be measured. The ramp occurs in $\frac{1}{10}$ second. As presently configured, the board co-averages these ramps to produce averaged spectra in time periods of up to one second. Other time periods can be easily implemented. It can be easily modified to co-average over any time period. However, it is possible also to fit each spectral scan to determine gas concentration.

Figure 5:
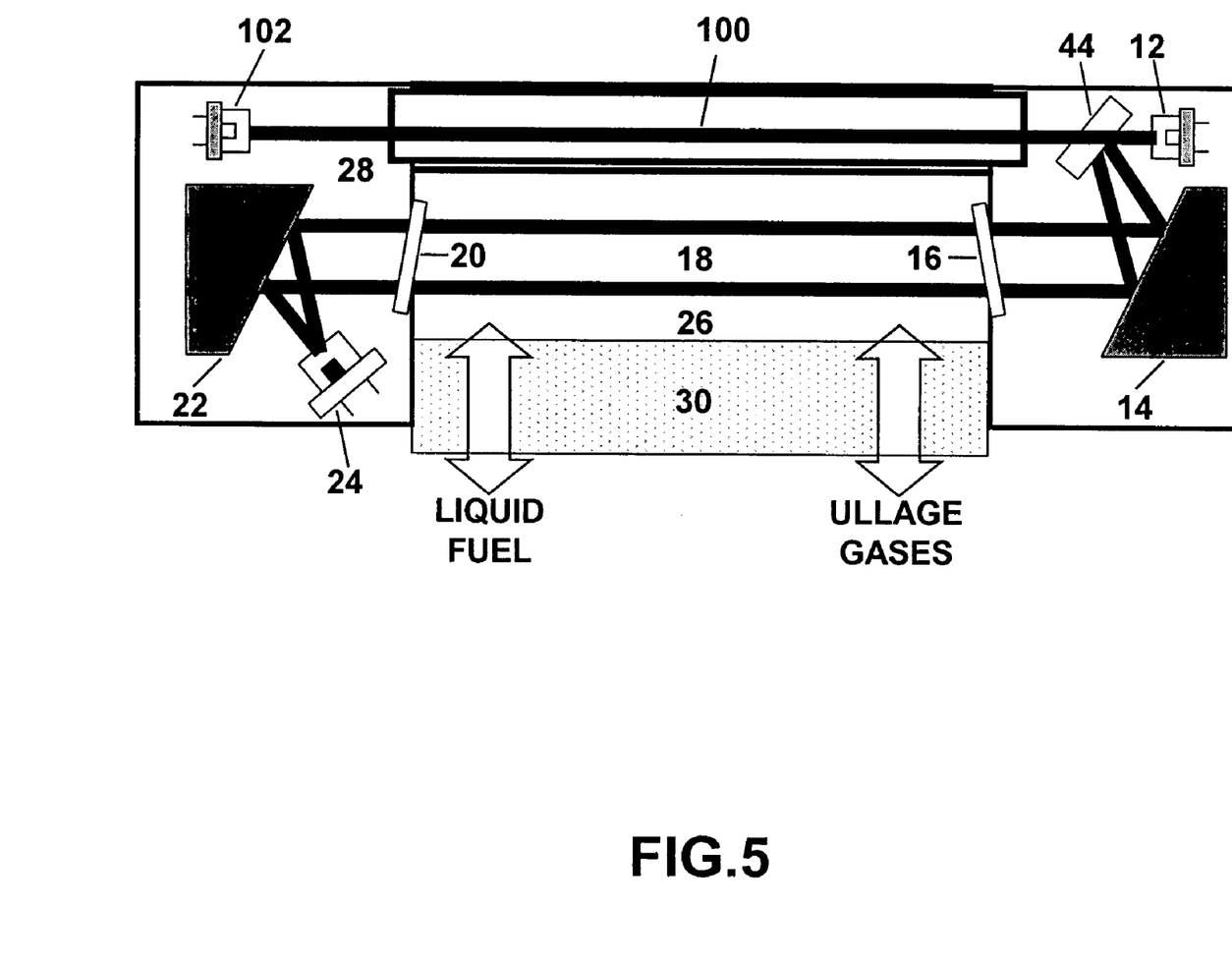
FIG. 5 is a schematic illustrating the use of a second photodiode detector to provide means to check the integrity of the sealed chamber that house the laser and photodiode detector.

Moreover, the invention provides a means to check the integrity of the sealed chamber 28 that houses the photodiode detector 24 and laser diode 12, to monitor the health of the laser system, and to monitor the noise level of the laser signal (FIG. 5). The laser beam is again split into two separate paths using a beamsplitter 44. In the first path 100, a portion of the laser light passes through the beamsplitter 44 and traverses the sealed chamber 28 to a photodiode detector 102 located on the other end of the chamber 28. Since the chamber is normally filled with an inert gas, there is no oxygen absorption in this path. In the event that one of the optical windows 16 and 20 cracks or one of the window seals breaks, ullage gases containing oxygen will leak into the sealed chamber 28. Such a leak will be immediately detected by the appearance of an oxygen absorption in this path. Upon detection of mechanical failures, the whole sensor system is shut down to prevent any live electrical wires from coming into contact with the ullage gases. A warning is also sent to the pilot. Mechanical failures are very unlikely, but precautionary measures are warranted. In addition, this optical path 100 can be used to monitor the noise level of the laser signal. This information can be used to adjust the averaging time of the measurements or used to determine the current sensitivity of the sensor system. In scenarios of total liquid immersion of the sensor head, measurements of oxygen concentrations are temporarily interrupted. This additional optical path helps the sensor system to differentiate between loss signals due to liquid immersion and actual system failures. Pressure and temperature sensors are not needed to quantify this particular measurement obtained from this internal path 100 since we are only interested in the presence of any sharp absorption peaks that depict the presence of oxygen. A pressure sensor can be also installed in the sealed chamber to monitor any drop in pressure that arises from ullage gases entering the said chamber due to cracked windows. Since the chamber is sealed with an inert gas at one atmosphere, a pressure reading much lower than this set pressure inside the chamber during flight (pressure at flight altitude is much lower than 1 atmosphere) is a clear indication of such mechanical failures.

In the modification of the preferred embodiment where a reference cell 40 is used (FIG. 2), the internal laser path can include a section 50 that is exposed to the inert gas filling the sealed chamber 28. The reference cell 40 should contain an oxygen concentration that is 5 percent or lower. Any leaks of ullage gases, due to mechanical failures of the optical windows 16 and 20, into the sealed chamber 28 will be detected by the section of this optical path length. A rise in the detected laser signal by the photodiode will be seen if ullage gases that contain oxygen at a concentration higher than the reference cell 40 enter the chamber 28. Furthermore, the sealed chamber 92 of the in-line sensor head 90 in FIG. 5 can incorporate an additional laser path using a beamsplitter and another photodiode detector for checking the integrity of the chamber.

Figure 6:
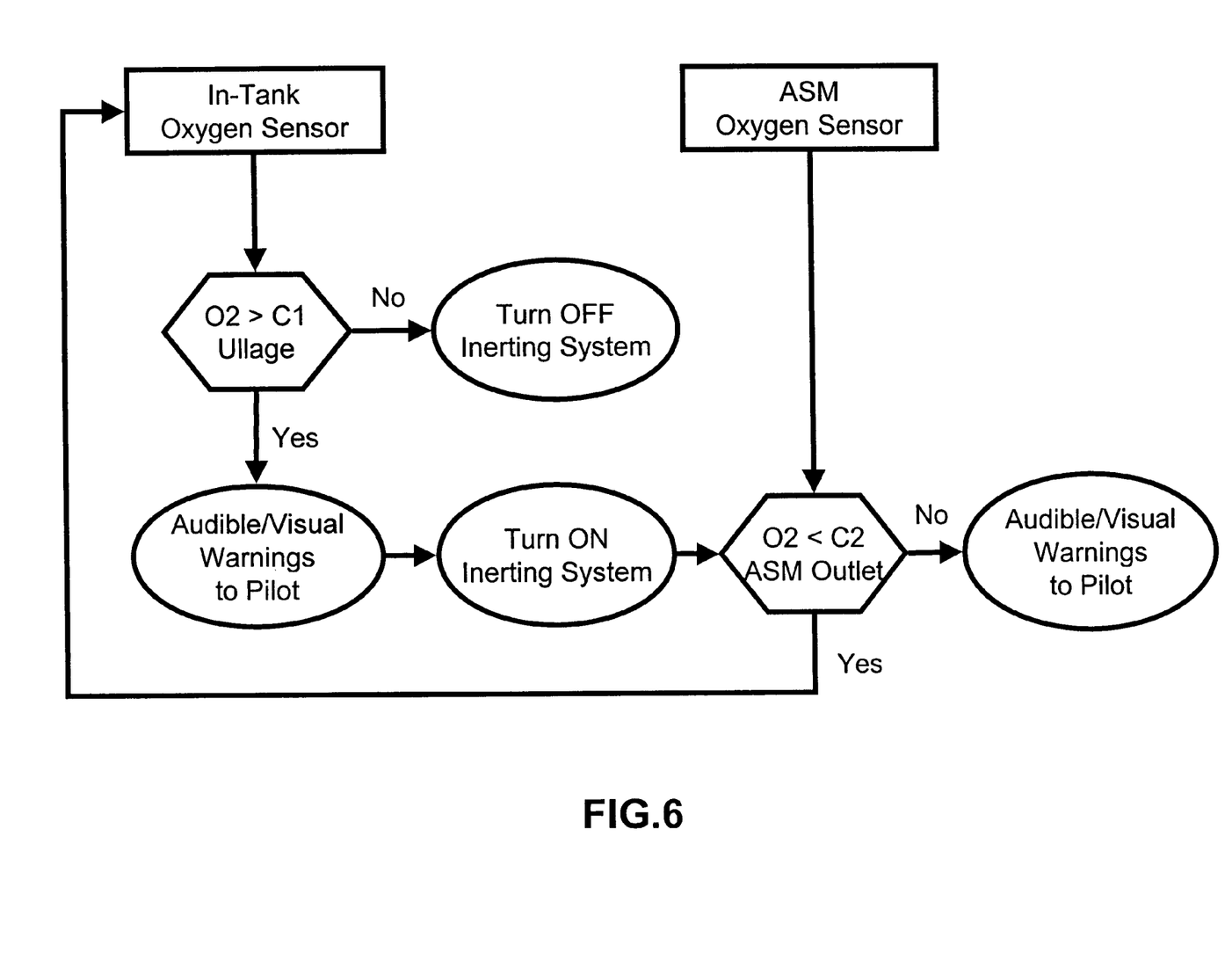
FIG. 6 illustrates the feedback control mechanism to turn on and off the inerting system based on the concentration measurements of oxygen in the ullage.

The invention also provides means to relate the measurements to the pilot and/or inerting systems for warning purposes and feedback controls. The sensor system can incorporate audible and/or visual and/or tactile signals to warn the operator (e.g., pilot) of impending failure of the inerting system and the presence of explosive mixtures in the fuel tanks (FIG. 6). A visual and/or audible warning can be strategically placed in the cockpit to warn the pilot of potential problems associated with the inerting systems. One such problems is when the oxygen concentration in the inerting gas exceeds a predetermined safe level (denoted by C2 in FIG. 6) Data from the in-tank sensor system can be relayed to the inerting systems for control purposes, such as shutting off the inerting system when the oxygen concentration inside the ullage of fuel tanks has reached a safe level (denoted by C1 in FIG. 6). Moreover, when the in-tank sensors (for oxygen and fuel level) are used in tandem with the ASM sensors (for oxygen and flow rate), the pilot can be notified of the time required to inert the ullage of fuel tanks to the desirable safe oxygen level. In-tank fuel level sensors quantify the remaining fuel level in the fuel tank compartments from which the volume of the ullage can be inferred from the known fuel capacity of each of the compartments. This volume is useful for computing the time required for the inerting system to purge the ullage gases to an acceptable oxygen level.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for monitoring oxygen concentrations in fuel tank ullage, said apparatus comprising a sensor head comprising:
   an optical cavity exposed to an ambient gaseous environment of a fuel tank or air separation module, wherein said optical cavity is at least partially encased in a metal foam;
   a laser light source emitting wavelength modulated light through said cavity;
   means for expediting removal of liquid droplets from surfaces of said apparatus through which said wavelength modulated light passes; and
   a detector receiving said wavelength modulated light.

2. The apparatus of claim 1 wherein said laser light source comprises a diode laser light source emitting wavelength modulated light modulated about an absorption wavelength of oxygen.

3. The apparatus of claim 2 wherein said laser light source comprises a vertical cavity surface emitting laser light source.

4. The apparatus of claim 1 wherein said detector comprises a photodiode detector.

5. The apparatus of claim 1 additionally comprising one or both of pressure and temperature sensors.

6. The apparatus of claim 1 additionally comprising an optical path extension apparatus in said cavity.

7. The apparatus of claim 6 wherein said optical path extension apparatus is selected from the group consisting of off-axis parabolic mirrors, retroreflectors, and multiple pass cells.

8. The apparatus of claim 1 additionally comprising a sealed reference cell containing a predetermined concentration of oxygen, a beamsplitter capturing a portion of said wavelength modulated light and directing it through said reference cell, and a second detector receiving said portion.

9. The apparatus of claim 1 wherein said laser light source comprise a fiber optic emission point.

10. The apparatus of claim 1 additionally comprising one or more sealed chambers housing said laser light source and said detector.

11. The apparatus of claim 10 additionally comprising a beamsplitter capturing a portion of said wavelength modulated light and directing it through said one or more chambers but not outside of said one or more chambers and a second detector receiving said portion.

12. A method for monitoring oxygen concentrations in fuel tank ullage, the method comprising the steps of:
providing a sensor head comprising an optical cavity, wherein the optical cavity is at least partially encased in a metal foam;
exposing the optical cavity to an ambient gaseous environment of a fuel tank or air separation module;
via a laser light source, emitting wavelength modulated light through the cavity;
providing for expeditious removal of liquid droplets from surfaces through which wavelength modulated light passes; and
receiving the wavelength modulated light with a detector.

13. The method of claim 12 wherein the laser light source comprises a diode laser light source emitting wavelength modulated light modulated about an absorption wavelength of oxygen.

14. The method of claim 13 wherein the laser light source comprises a vertical cavity surface emitting laser light source.

15. The method of claim 12 wherein the detector comprises a photodiode detector.

16. The method of claim 12 additionally comprising one or both of measuring pressure of the ambient gaseous environment and measuring temperature of the ambient gaseous environment.

17. The method of claim 12 additionally comprising extending an optical path in the cavity.

18. The method of claim 17 wherein the extending step comprises employing one or more of the group consisting of off-axis parabolic mirrors, retroreflectors, and multiple pass cells.

19. The method of claim 12 additionally comprising providing a sealed reference cell containing a predetermined concentration of oxygen, a beamsplitter capturing a portion of the wavelength modulated light and directing it through the reference cell, and a second detector receiving the portion.

20. The method of claim 12 wherein the laser light source comprise a fiber optic emission point.

21. The method of claim 12 additionally comprising providing one or more sealed chambers housing the laser light source and the detector.

22. The method of claim 21 additionally comprising employing a beamsplitter to capture a portion of the wavelength modulated light, directing the portion through the one or more chambers but not outside of the one or more chambers, and receiving the portion with a second detector.

* * * * *